United States Patent [19]
Polin

[11] 3,949,068
[45] Apr. 6, 1976

[54] PHARMACEUTICAL COMPOSITIONS
[75] Inventor: Herbert S. Polin, Geneva, Switzerland
[73] Assignee: University of Alabama in Birmingham Medical and Educational Foundation, Birmingham, Ala.
[22] Filed: Aug. 18, 1970
[21] Appl. No.: 64,796

Related U.S. Application Data
[62] Division of Ser. No. 346,106, Feb. 20, 1964, Pat. No. 3,538,216.

[52] U.S. Cl. .................................................. 424/79
[51] Int. Cl.$^2$......................................... A61K 31/74
[58] Field of Search ...................................... 424/79

Primary Examiner—Stanley J. Friedman
Attorney, Agent, or Firm—Pollock, Vande Sande & Priddy

[57] ABSTRACT

Injectable emulsion containing a medicament, a thixotropic agent and membrane-forming substance having ion-exchange properties. The membrane-forming substance being a polymerizable monomer which polymerizes by reaction with a polymerizing agent.

10 Claims, No Drawings

PHARMACEUTICAL COMPOSITIONS

This is a division of my prior copending application Ser. No. 346,106, filed Feb. 20, 1964, and now U.S. Pat. No. 3,538,216.

This invention relates to novel pharmaceutical compositions in liquid form. More particularly, it is concerned with new and useful liquid injectable items of the foregoing type which have as their object the controlled release of a drug.

This is accomplished by the injection of a coated or enrobed solution whereby the drug diffuses slowly through a liquid or plastic membrane. More specifically, injectables suitable for animal use are stabilized by the process of enrobing the active ingredient in solution form with a liquid envelope of such a nature that when injected into the animal, it provides a continuous external phase and so results in a controlled or reduced and constant rate of diffusion of the active ingredient through the membrane. Hence, the use of this invention now makes possible for the first time a sustained-release effect for a drug when parenterally administered due to the delayed release of the active ingredient caused by its controlled diffusion through a semi-permeable membrane as aforementioned.

Concerning the matter of a sustained action intramuscular dosage form in more detail, it is to be understood that the liquid colloidal membrane must be a substance which will not reside at the site of injection for a prolonged period of time and cause necrosis or any other problem. Furthermore, the rate of adsorption of the colloidal membrane must be slower than the rate of the drug in order for the sustained-release effect to be attained in the first place. In addition, the factor of safety must also necessarily be considered when dealing with problems of this type. Among the various liquids with a membraneous outer phase, there exist a wide variety of synthetic and natural substances which satisfy all these requirements and are at the same time compatible with internal living tissue. The principle exposed has been applied to such diverse types of drugs as a salt, such as sodium chloride, as well as to antibiotics such as oxytetracycline hydrochloride and the like, in addition to enzymes, hormones, tranquilizers, and so forth.

In accordance with a more specific embodiment of the present invention, the instant compositions comprise a thixotropic agent, a gelatinous oil membrane admixed with ion-exchange agents and a water-soluble antibiotic as the drug. The gelatinous oil membrane, of course, encompasses both the thixotropic agent as well as the aforesaid medicament. A thixotropic agent in this connection is defined to mean an agent which assists in maintaining or re-establishing the integrity of the emulsion both during and after injection of same when it contains the enrobed drug. For the present purposes, it must be selected from a group of chemical agents having little or no toxicity and at the same time, it must be effective in these compositions for the reason intended as previously stated, i.e., it must permit injection of the composition as a fluid and subsequent jelling in the muscle thereafter. Examples of such substances include Cabocil, carboxymethylcellulose, bentonite, agar, and so forth, and they must be present in the system in an amount which is sufficient to give a gel having the appropriate rheological properties, e.g., a minor amount such as 5% or less. A preferred form of thixotropic agent for use in this connection would be the aforementioned Cabocil, which is the registered trademark name of the Cabot Corporation of Boston, Mass. for a dry silica of extremely fine particle size.

The oil-gelatin composition, on the other hand, is most desirably a mixture of an unsaturated vegetable oil and a proteinaceous material, while the preferred ion-exchange material is usually of the Rohm & Haas Amberlite variety, in which case, it would specifically be sulfonic acid type like a polystyrene sulfonic acid in cation form. Examples of such oils which have the required membrane-forming properties and which have been used to envelope drugs in accordance with the disclosed invention are linseed oil, oiticica oil, castor oil, safflower oil, corn oil, etc. These oils may be readily modified in situ to the form of resistant and permaselective membranes by such means as pH modification, oxidation, heat treatment, and the like. The proteinaceous material may be a form of natural polymer like gelatin and be non-toxic in nature and preferably biodegradable like oxidized or refined gelatin. Examples of other suchlike substances for use here include corn starch and lecithin, for instance, as well as the white of eggs, casein, soybean, etc. As a matter of fact, any membrane-forming substance, such as a polypeptide derived by hydrolysis or enzymatic degradation from the nitrogenous constituent of vegetable and animal sources, can be used here for the purposes at hand with more than satisfactory results being achieved.

Examples of applicable drugs or of the medicament components of this invention are, as previously indicated, sodium chloride in the case of an inorganic salt and oxytetracycline hydrochloride in the case of an antibiotic or, and even more specifically in the latter case, the magnesium chloride complex of oxytetracycline hydrochloride in an aqueous propylene glycol solvent system. Needless to say, the drug must always be found soluble in the muscle fluids into which it is injected after parenteral administration. Other examples of drug applications found useful in this connection include injectable iron compounds, as well as injectable anthelmintics when used in place of the aforementioned sodium chloride or oxytetracycline hydrochloride complex. Other tetracycline-type antibiotic acid addition salts can also be used here instead of the two aforementioned respective specific examples. Further, such medicaments as papain, hydrocortisone, prednisolone, meclizine and reserpine are examples of still other pharmaceutical drug items which find application here, as previously indicated in a more generic sense under the heading of enzymes, hormones, tranquilizers and so forth, respectively. The present, injectable pharmaceutical compositions can, of course, be administered in any of the ways standard to commonly acceptable pharmaceutical practice, as generally recognized by those skilled in the art. This would also include the use of newer forms of injectable sprays, whereby the stabilized injectable solution is parenterally administered in this manner with a minimum of inconvenience to the patient.

In summary, therefore, the essential concept of this invention is that of a physical-chemical process by which the diffusion of an enrobed drug or enveloped chemical can be controlled and maintained at a constant rate. As previously indicated, the materials for accomplishing this task are varied, it being only their properties in combination for supporting the objectives of the process that play an important role. Thus, for instance, proteins, synthetic or natural monomers, filmforming natural or synthetic oils, gelatins, lecithin, and the like, may all be adapted for use. Of course, it is important that any composition used to be compatible with the host living system and indeed, some of the chemicals operating to modify the composition to function as a diffusion membrane are found as natural constituents of living systems. For example, in the instance where a liquid protein such as the white of egg is used as a constituent in the membrane composition, it may be hardened after injection to any desirable degree by following its injection with a second injection of a coagulant of a desired hydrogen ion concentration, such as acetic acid, or dependence upon the pH at the site of injection will provide the desired modification.

More particularly, monomers of natural or synthetic substances may be injected so that a subsequent polymerization provides the desired diffusion envelope. The monomer may be injected with an accompanying polymer-forming substance plus a retardent so that polymerization occurs at a selected time delay after injection, or the monomer may be selected from a group of substances which coact with body constituents available at the site of injection so as to form a membraneous polymer enveloping the drug. Alternatively, the injection may be administered in two stages; for instance, the drug and monomer first plus other control constituents, followed by the injection of the polymerizing agent. Examples of substances found in the body and which may assist in the formation of polymers are: the aldols, aldosterine, the aldehydes, aldol condensation products, aldehyde resins, the electrolytes, the lipids, etc.

This invention is further illustrated by the following examples, which are not to be construed in any manner or way as imposing limitations upon the scope thereof. On the contrary, it is to be clearly understood that resort may be had to various other embodiments, modifications and equivalents thereof which readily suggest themselves to those skilled in the art without departing from the spirit of the present invention and/or the scope of the appended claims.

EXAMPLE I

An injectable pharmaceutical composition useful for intramuscular administration is prepared by grinding together in a paint mill 5 g. of Amberlite IR-120 (the registered trademark name of the Rohm & Haas Company of Philadelphia, Pa. for a polystyrene sulfonic acid ion-exchange material in sodium cation form) and 5 g. of Cabocil in 35 g. of castor oil until a stable suspension is achieved. At this point, 50 g. of solution containing 125 mg. of oxytetracycline hydrochloride per ml. of 20% aqueous propylene glycol solution (Pfizer Terramycin intramuscular solution is used here where the antibiotic is complexed as the magnesium chloride complex salt) and 1.5 g. of water-soluble gelatin dissolved in 3.5 g. of distilled water are prepared and mixed with the suspension in a colloid mill until a stable emulsion is achieved. When the thus obtained composition is injected into the muscle of an animal, the rate of release of the antibiotic is approximately 1% of the active substance per hour.

Example II

The procedure described in Example I is repeated except that the oxytetracycline hydrochloride component is now used in dry form, with comparable results being obtained. In like manner, other tetracycline-type antibiotics are employed in place of this particular drug, such as tetracycline, chlortetracycline, bromtetracycline, 6-demethylchlortetracycline, 6-demethyl-6-deoxytetracycline, 6-demethyl-6-deoxy-7-bromtetracycline, with comparable results also being obtained in each case.

EXAMPLE III

The procedure described in Example I is repeated employing other unsaturated vegetable oils in place of castor oil. Among the specific oils which have been used are safflower oil, linseed oil, corn oil and oiticia oil. The results obtained in each case are comparable with those obtained with castor oil.

EXAMPLE IV

The procedure described in Example I is repeated using other proteinaceous materials in place of gelatin. Among those which have been used are corn starch, lecithin, egg white, casein and soybean, and the results obtained in each case are similar to those obtained using the gelatin.

EXAMPLE V

The procedure described in Example I is repeated using other thixotropic agents in place of Cabocil under the conditions tested. Included among the agents tested are carboxymethylcellulose (CMC), bentonite and agar. In each case, the results obtained are similar to those afforded with the Carbocil.

EXAMPLE VI

The procedure described in Example I is repeated using other sulfonic acid resin materials in place of Amberlite IRC-120 as the ion-exchange material of choice. Thus, for instance, when Permutit Q (a polystyrene sulfonic acid resin in sodium cation form produced by the Permutit Company of New York, N.Y.) is used in place of the aforementioned Amberlite material, the results obtained are substantially the same.

What is claimed is:

1. In an injectable medicament-bearing emulsion for treatment of animal tissue, which tissue contains fluids in which the medicament is soluble, the improvement which is characterized in that the emulsion contains a minor effective amount of a thixotropic agent and a membrane-forming substance having ion-exchange properties wherein the membrane-forming substance is a polymerizable monomer which polymerizes by reaction with a polymerizing agent at the site of injection into said animal tissue to form a longer chain molecule, whereby the medicament may be diffused at a sustained, constant rate into said fluids.

2. The composition of claim 1 wherein the polymerizable monomer is a substance which coacts with tissue substituents at the site of injection so as to form a semipermeable polymeric membrane which envelopes both the thixotropic agent and the medicament.

3. The composition of claim 1 wherein the polymer-forming substance is already present therein prior to injection together with a retardant.

4. The composition of claim 1 wherein the polymerizing agent is an aldol.

5. The composition of claim 1 wherein said polymerizing agent is aldosterone.

6. The composition of claim 1 wherein the polymerizing agent is an aldehyde.

7. The composition of claim 1 wherein the polymerizing agent is an aldol condensation product.

8. The composition of claim 1 wherein the polymerizing agent is an aldehyde resin.

9. The composition of claim 1 wherein the polymerizing agent is an electrolyte.

10. The composition of claim 1 wherein the polymerizing agent is a lipid.

* * * * *